United States Patent
Chinta et al.

(10) Patent No.: US 12,006,280 B2
(45) Date of Patent: *Jun. 11, 2024

(54) METHANOL PRODUCTION PROCESS WITH HIGHER CARBON UTILIZATION BY $CO_2$ RECYCLE

(71) Applicant: ENI S.p.A., Rome (IT)

(72) Inventors: Sivadinarayana Chinta, Sugar Land, TX (US); Ravichander Narayanaswamy, Bengaluru (IN); Atul Pant, Bengaluru (IN)

(73) Assignee: ENI S.P.A., Rome (IT)

( * ) Notice: Subject to any disclaimer, the term of this patent is extended or adjusted under 35 U.S.C. 154(b) by 188 days.

This patent is subject to a terminal disclaimer.

(21) Appl. No.: 17/424,722

(22) PCT Filed: Jan. 2, 2020

(86) PCT No.: PCT/US2020/012035
§ 371 (c)(1),
(2) Date: Jul. 21, 2021

(87) PCT Pub. No.: WO2020/154075
PCT Pub. Date: Jul. 30, 2020

(65) Prior Publication Data
US 2021/0387934 A1 Dec. 16, 2021

Related U.S. Application Data

(60) Provisional application No. 62/794,843, filed on Jan. 21, 2019.

(51) Int. Cl.
*C07C 29/151* (2006.01)
*B01D 3/14* (2006.01)
(Continued)

(52) U.S. Cl.
CPC .......... *C07C 29/1518* (2013.01); *B01D 3/143* (2013.01); *B01D 53/002* (2013.01);
(Continued)

(58) Field of Classification Search
CPC ................ C07C 29/1518; C07C 31/04; C01B 2203/0238; C01B 2203/0261;
(Continued)

(56) References Cited

U.S. PATENT DOCUMENTS 5,179,129 A    1/1993  Studer
11,834,394 B2  12/2023 Alahmadi et al.
(Continued)

FOREIGN PATENT DOCUMENTS

CN    101184714 A      5/2008
WO    2005108336 A1   11/2005
(Continued)

OTHER PUBLICATIONS

Chinese Office Action for Chinese Application No. 202080021745.X, dated Apr. 1, 2023, 12 pages with translation.
(Continued)

*Primary Examiner* — Jafar F Parsa
(74) *Attorney, Agent, or Firm* — CANTOR COLBURN LLP

(57) ABSTRACT

A process for producing methanol includes the following steps (a) reacting, via a catalytic partial oxidation (CPO) reaction, a CPO reactant mixture (hydrocarbon, oxygen, and optionally steam) in a CPO reactor to produce syngas including $H_2$, CO, $CO_2$, $H_2O$, and unreacted hydrocarbons; and wherein the CPO reactor includes a CPO catalyst; (b) introducing the syngas to a methanol reactor to produce a methanol reactor effluent stream (methanol, water, hydrogen, carbon monoxide, carbon dioxide, and hydrocarbons); and (c) separating the methanol reactor effluent stream into
(Continued)

a crude methanol stream, a hydrogen stream, a $CO_2$ stream, and a purge gas stream. The crude methanol stream comprises includes methanol and water; wherein the purge gas stream includes carbon monoxide and hydrocarbons; and the CO2 stream includes at least a portion of the CO2 of the methanol reactor effluent stream; and (d) recycling at least a portion of the CO2 stream to the CPO reactor.

20 Claims, 1 Drawing Sheet

(51) Int. Cl.
- B01D 53/00 (2006.01)
- B01D 53/047 (2006.01)
- B01D 53/14 (2006.01)
- B01D 53/22 (2006.01)
- B01D 53/26 (2006.01)
- C01B 3/38 (2006.01)

(52) U.S. Cl.
CPC ....... *B01D 53/047* (2013.01); *B01D 53/1437* (2013.01); *B01D 53/1443* (2013.01); *B01D 53/1475* (2013.01); *B01D 53/229* (2013.01); *B01D 53/265* (2013.01); *C01B 3/386* (2013.01); *B01D 2252/20405* (2013.01); *B01D 2252/20484* (2013.01); *B01D 2257/108* (2013.01); *B01D 2257/504* (2013.01); *C01B 2203/0238* (2013.01); *C01B 2203/0261* (2013.01); *C01B 2203/0405* (2013.01); *C01B 2203/0415* (2013.01); *C01B 2203/043* (2013.01); *C01B 2203/046* (2013.01); *C01B 2203/061* (2013.01)

(58) Field of Classification Search
CPC .... C01B 2203/0405; C01B 2203/0415; C01B 2203/046; C01B 2203/061
See application file for complete search history.

(56) References Cited

U.S. PATENT DOCUMENTS

| | | |
|---|---|---|
| 2004/0171701 A1 | 9/2004 | Shaw |
| 2005/0107481 A1 | 5/2005 | Janssen et al. |
| 2007/0282018 A1 | 12/2007 | Jenkins et al. |
| 2008/0161428 A1 | 7/2008 | Strait |
| 2008/0220489 A1 | 9/2008 | Offerman |
| 2010/0076238 A1 | 3/2010 | Brandvold et al. |
| 2014/0323598 A1 | 10/2014 | Chakravarti et al. |
| 2014/0357736 A1 | 12/2014 | Dahl |
| 2016/0060109 A1 | 3/2016 | Chakravarti et al. |
| 2022/0119328 A1 | 4/2022 | Schroer et al. |

FOREIGN PATENT DOCUMENTS

| | | |
|---|---|---|
| WO | 2013102589 A1 | 7/2013 |
| WO | 2017065613 A1 | 4/2017 |
| WO | 2018234971 | 12/2018 |
| WO | 2018234971 A1 | 12/2018 |

OTHER PUBLICATIONS

Extended European Search Report dated Sep. 28, 2022 re: Application No. PCT/US2020/012035, pp. 1-7, US 2004/0171701 A1, WO 2017/065613 A1 and WO 2013/102589 A1.

International Search Report dated May 28, 2020 re: Application No. PCT/US2020/012035, pp. 1-4, citing: US 2007-0282018 A1, US 2008-0220489 A1, US 2016-0060109 A1, WO 2018-234971 A1, WO 2017-065613 A1.

Written Opinion dated May 28, 2020 re: Application No. PCT/US2020/012035, pp. 1-7, citing: US 2007-0282018 A1, US 2008-0220489 A1, US 2016-0060109 A1 and WO 2018-234971 A1.

International Search Report dated Jun. 2, 2020 re: Application No. PCT/US2020/014395, pp. 1-3, citing: WO 2018-234971 A1, U.S. Pat. No. 5,179,129 A, US 2010-0076238 A1, US 2008-161428 A1, WO 2005-108336 A1.

Written Opinion dated Jun. 2, 2020 re: Application No. PCT/US2020/014395, pp. 1-7, citing: WO 2018-234971 A1 and U.S. Pat. No. 5,179,129 A.

U.S. Non-Final Office Action for U.S. Appl. No. 17/424,714, dated Jan. 26, 2024, 20 pages.

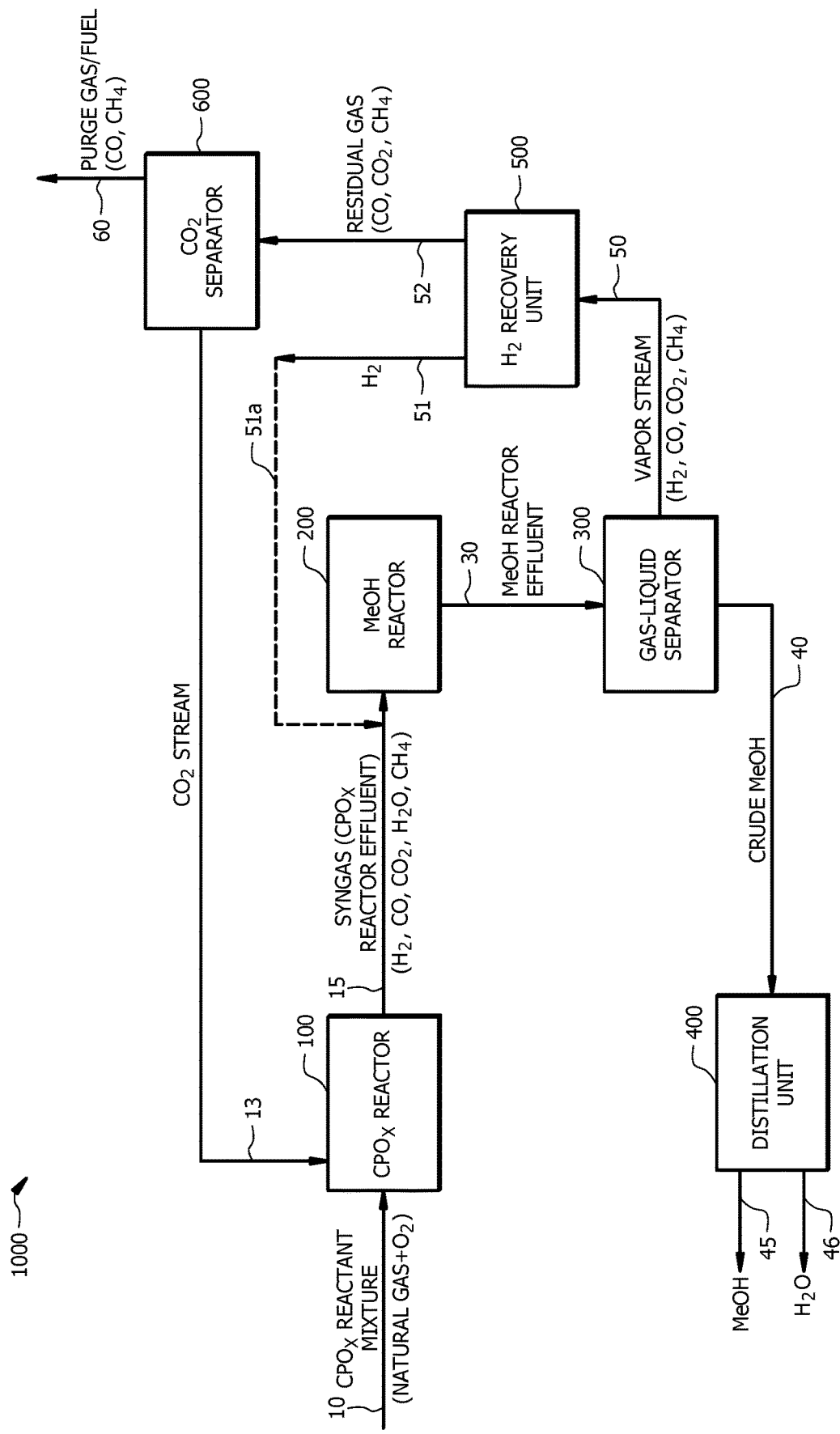

METHANOL PRODUCTION PROCESS WITH HIGHER CARBON UTILIZATION BY $CO_2$ RECYCLE

TECHNICAL FIELD

The present disclosure relates to methods of producing methanol, more specifically methods of producing methanol from syngas produced by catalytic partial oxidation of hydrocarbons, such as methane.

BACKGROUND

Synthesis gas (syngas) is a mixture comprising carbon monoxide (CO) and hydrogen ($H_2$), as well as small amounts of carbon dioxide ($CO_2$), water ($H_2O$), and unreacted methane ($CH_4$). Syngas is generally used as an intermediate in the production of methanol and ammonia, as well as an intermediate in creating synthetic petroleum to use as a lubricant or fuel.

Syngas is produced conventionally by steam reforming of natural gas (steam methane reforming or SMR), although other hydrocarbon sources can be used for syngas production, such as refinery off-gases, naphtha feedstocks, heavy hydrocarbons, coal, biomass, etc. SMR is an endothermic process and requires significant energy input to drive the reaction forward. Conventional endothermic technologies such as SMR produce syngas with a hydrogen content greater than the required content for methanol synthesis. Generally, SMR produces syngas with an M ratio ranging from 2.6 to 2.98, wherein the M ratio is a molar ratio defined as ($H_2$—$CO_2$)/(CO+$CO_2$).

In an autothermal reforming (ATR) process, a portion of the natural gas is burned as fuel to drive the conversion of natural gas to syngas resulting in relatively low hydrogen and high $CO_2$ concentrations. Conventional methanol production plants utilize a combined reforming (CR) technology that pairs SMR with autothermal reforming (ATR) to reduce the amount of hydrogen present in syngas. ATR produces a syngas with a hydrogen content lower than the required content for methanol synthesis. Generally, ATR produces syngas with an M ratio ranging from 1.7 to 1.84. In the CR technology, the natural gas feed volumetric flowrate to the SMR and the ATR can be adjusted to achieve an overall syngas M ratio of 2.0 to 2.06. Further, CR syngas has a hydrogen content greater than the required content for methanol synthesis. Furthermore, SMR is a highly endothermic process, and the endothermicity of the SMR technology requires burning fuel to drive the syngas synthesis. Consequently, the SMR technology reduces the energy efficiency of the methanol synthesis process.

Syngas can also be produced (non-commercially) by catalytic partial oxidation (CPO or CPOx) of natural gas. CPO processes employ partial oxidation of hydrocarbon feeds to syngas comprising CO and $H_2$. The CPO process is exothermic, thus eliminating the need for external heat supply (as opposed to SMR). However, the composition of the conventionally produced syngas is not suitable for methanol synthesis, for example, owing to the hydrogen to CO molar ratio. Conventional CPO processes can lead to the formation of coke deposited on the catalyst bed, which can further lead to catalyst deactivation and pressure swings in the reactor, making it difficult to operate the reactor continuously. Thus, there is an ongoing need for the development of syngas production processes by CPO.

BRIEF DESCRIPTION OF THE DRAWINGS

For a detailed description of the preferred aspects of the disclosed methods, reference will now be made to the accompanying drawing in which:

The FIGURE displays a schematic of a system for a methanol production process.

DETAILED DESCRIPTION

Disclosed herein are processes for producing methanol comprising (a) reacting, via a catalytic partial oxidation (CPO) reaction, a CPO reactant mixture in a CPO reactor to produce syngas; wherein the CPO reactant mixture comprises hydrocarbons and oxygen; wherein the CPO reactor comprises a single reaction zone, wherein the single reaction zone comprises a CPO catalyst; and wherein the syngas comprises hydrogen ($H_2$), carbon monoxide (CO), carbon dioxide ($CO_2$), water ($H_2O$), and unreacted hydrocarbons; (b) introducing at least a portion of the syngas (e.g., subsequent to cooling and water removal from syngas; and/or subsequent to pressure and/or syngas temperature adjustment) to a methanol reactor to produce a methanol reactor effluent stream; wherein the methanol reactor effluent stream comprises methanol, water, hydrogen, carbon monoxide, carbon dioxide, and hydrocarbons; (c) separating at least a portion of the methanol reactor effluent stream into a crude methanol stream, a hydrogen stream, a $CO_2$ stream, and a purge gas stream; wherein the crude methanol stream comprises methanol and water; wherein the purge gas stream comprises carbon monoxide and hydrocarbons; and wherein the $CO_2$ stream comprises at least a portion of the $CO_2$ of the methanol reactor effluent stream; and (d) recycling at least a portion of the $CO_2$ stream to the CPO reactor. The hydrocarbons used for syngas production can comprise methane, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, and the like, or combinations thereof.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

As used herein, the terms "$C_x$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof.

As used herein, the term "$C_{x+}$ hydrocarbons" refers to any hydrocarbon having equal to or greater than x carbon atoms (C). For example, the term "$C_2$ hydrocarbons" refers to any hydrocarbons having 2 or more carbon atoms, such as ethane, ethylene, $C_a$s, $C_4$s, $C_5$s, etc.

Referring to the FIGURE, a methanol production system 1000 is disclosed. The methanol production system 1000 generally comprises a catalytic partial oxidation (CPO or CPOx) reactor 100; a methanol reactor 200; a gas-liquid separator 300; a distillation unit 400; a hydrogen ($H_2$) recovery unit 500; and a carbon dioxide ($CO_2$) separator 600. As will be appreciated by one of skill in the art, and with the help of this disclosure, methanol production system components shown in the FIGURE can be in fluid communication with each other (as represented by the connecting lines indicating a direction of fluid flow) through any suitable conduits (e.g., pipes, streams, etc.).

In an aspect, a process for producing methanol as disclosed herein can comprise a step of reacting, via a CPO reaction, a CPO reactant mixture 10 in the CPO reactor 100 to produce syngas (e.g., CPO reactor effluent) 15; wherein the CPO reactant mixture 10 comprises hydrocarbons, oxygen, and optionally steam; wherein the CPO reactor 100 comprises a single reaction zone, wherein the single reaction zone comprises a CPO catalyst; and wherein the syngas 15 comprises hydrogen, carbon monoxide, carbon dioxide, water, and unreacted hydrocarbons.

Generally, the CPO reaction is based on partial combustion of fuels, such as various hydrocarbons, and in the case of methane, CPO can be represented by equation (1):

$$CH_4 + 1/2\ O_2 \rightarrow CO + 2H_2 \quad (1)$$

Without wishing to be limited by theory, side reactions can take place along with the CPO reaction depicted in equation (1); and such side reactions can produce carbon dioxide ($CO_2$) and water ($H_2O$), for example via hydrocarbon combustion, which is an exothermic reaction. As will be appreciated by one of skill in the art, and with the help of this disclosure, and without wishing to be limited by theory, the CPO reaction as represented by equation (1) can yield a syngas with a hydrogen to carbon monoxide ($H_2/CO$) molar ratio having the theoretical stoichiometric limit of 2.0. Without wishing to be limited by theory, the theoretical stoichiometric limit of 2.0 for the $H_2/CO$ molar ratio means that the CPO reaction as represented by equation (1) yields 2 moles of $H_2$ for every 1 mole of CO, i.e., $H_2/CO$ molar ratio of (2 moles $H_2$/1 mole CO)=2. As will be appreciated by one of skill in the art, and with the help of this disclosure, the theoretical stoichiometric limit of 2.0 for the $H_2/CO$ molar ratio in a CPO reaction cannot be achieved practically because reactants (e.g., hydrocarbons, oxygen) as well as products (e.g., $H_2$, CO) undergo side reactions at the conditions used for the CPO reaction. As will be appreciated by one of skill in the art, and with the help of this disclosure, and without wishing to be limited by theory, in the presence of oxygen, CO and $H_2$ can be oxidized to $CO_2$ and $H_2O$, respectively. The relative amounts (e.g., composition) of CO, $H_2$, $CO_2$ and $H_2O$ can be further altered by the equilibrium of the water-gas shift (WGS) reaction, which will be discussed in more detail later herein. The side reactions that can take place in the CPO reactor 100 can have a direct impact on the M ratio of the produced syngas, wherein the M ratio is a molar ratio defined as ($H_2$—$CO_2$)/(CO+$CO_2$). In the absence of any side reaction (theoretically), the CPO reaction as represented by equation (1) results in a syngas with an M ratio of 2.0. However, the presence of side reactions (practically) reduces $H_2$ and increases $CO_2$, thereby resulting in a syngas with an M ratio below 2.0.

Further, without wishing to be limited by theory, the CPO reaction as depicted in equation (1) is an exothermic heterogeneous catalytic reaction (i.e., a mildly exothermic reaction) and it occurs in a single reactor unit (e.g., in a single stage process in a single reaction zone), such as the CPO reactor 100 (as opposed to more than one reactor unit as is the case in conventional processes for syngas production, such as steam methane reforming (SMR)—autothermal reforming (ATR) combinations). While it is possible to conduct partial oxidation of hydrocarbons as a homogeneous reaction, in the absence of a catalyst, homogeneous partial oxidation of hydrocarbons process entails excessive temperatures, long residence times, as well as excessive coke formation, which strongly reduce the controllability of the partial oxidation reaction, and may not produce syngas of the desired quality in a single reactor unit (e.g., in a single stage process in a single reaction zone).

Furthermore, without wishing to be limited by theory, the CPO reaction is fairly resistant to chemical poisoning, and as such it allows for the use of a wide variety of hydrocarbon feedstocks, including some sulfur containing hydrocarbon feedstocks; which, in some cases, can enhance catalyst life-time and productivity. By contrast, conventional ATR processes have more restrictive feed requirements, for example in terms of content of impurities in the feed (e.g., feed to ATR is desulfurized), as well as hydrocarbon composition (e.g., ATR primarily uses $CH_4$-rich feed).

In an aspect, the hydrocarbons suitable for use in a CPO reaction as disclosed herein can include methane ($CH_4$), natural gas, natural gas liquids, associated gas, well head gas, enriched gas, paraffins, shale gas, shale liquids, fluid catalytic cracking (FCC) off gas, refinery process gases, stack gases, fuel gas from fuel gas header, and the like, or combinations thereof. The hydrocarbons can include any suitable hydrocarbons source, and can contain $C_1$-$C_6$ hydrocarbons, as well some heavier hydrocarbons.

In an aspect, the CPO reactant mixture 10 can comprise natural gas. Generally, natural gas is composed primarily of methane, but can also contain ethane, propane and heavier hydrocarbons (e.g., iso-butane, n-butane, iso-pentane, n-pentane, hexanes, etc.), as well as very small quantities of nitrogen, oxygen, carbon dioxide, sulfur compounds, and/or water. The natural gas can be provided from a variety of sources including, but not limited to, gas fields, oil fields, coal fields, fracking of shale fields, biomass, landfill gas, and the like, or combinations thereof. In some aspects, the CPO reactant mixture 10 can comprise $CH_4$ and $O_2$.

The natural gas can comprise any suitable amount of methane. In some aspects, the natural gas can comprise biogas. For example, the natural gas can comprise from about 45 mol % to about 80 mol % methane, from about 20 mol % to about 55 mol % carbon dioxide, and less than about 15 mol % nitrogen.

In an aspect, natural gas can comprise $CH_4$ in an amount of equal to or greater than about 45 mol %, alternatively equal to or greater than about 50 mol %, alternatively equal to or greater than about 55 mol %, alternatively equal to or greater than about 60 mol %, alternatively equal to or greater than about 65 mol %, alternatively equal to or greater than about 70 mol %, alternatively equal to or greater than about 75 mol %, alternatively equal to or greater than about 80 mol %, alternatively equal to or greater than about 82 mol %, alternatively equal to or greater than about 84 mol %, alternatively equal to or greater than about 86 mol %, alternatively equal to or greater than about 88 mol %, alternatively equal to or greater than about 90 mol %, alternatively equal to or greater than about 91 mol %, alternatively equal to or greater than about 92 mol %, alternatively equal to or greater than about 93 mol %, alternatively equal to or greater than about 94 mol %, alternatively equal to or greater than about 95 mol %, alternatively equal to or greater than about 96 mol %, alternatively equal to or greater than about 97 mol %, alternatively equal to or greater than about 98 mol %, or alternatively equal to or greater than about 99 mol %.

In some aspects, the hydrocarbons suitable for use in a CPO reaction as disclosed herein can comprise $C_1$-$C_6$ hydrocarbons, nitrogen (e.g., from about 0.1 mol % to about 15 mol %, alternatively from about 0.5 mol % to about 11 mol %, alternatively from about 1 mol % to about 7.5 mol %, or alternatively from about 1.3 mol % to about 5.5 mol %), and carbon dioxide (e.g., from about 0.1 mol % to about 2 mol %, alternatively from about 0.2 mol % to about 1 mol %, or alternatively from about 0.3 mol % to about 0.6 mol %). For example, the hydrocarbons suitable for use in a CPO reaction as disclosed herein can comprise $C_1$ hydrocarbon (about 89 mol % to about 92 mol %); $C_2$ hydrocarbons (about 2.5 mol % to about 4 mol %); $C_3$ hydrocarbons (about 0.5 mol % to about 1.4 mol %); $C_4$ hydrocarbons (about 0.5 mol % to about 0.2 mol %); $C_5$ hydrocarbons (about 0.06 mol %); and $C_6$ hydrocarbons (about 0.02 mol %); and optionally nitrogen (about 0.1 mol % to about 15 mol %), carbon dioxide (about 0.1 mol % to about 2 mol %), or both nitrogen (about 0.1 mol % to about 15 mol %) and carbon dioxide (about 0.1 mol % to about 2 mol %).

The oxygen used in the CPO reactant mixture 10 can comprise 100% oxygen (substantially pure $O_2$), oxygen gas (which may be obtained via a membrane separation process), technical oxygen (which may contain some air), air, oxygen enriched air, oxygen-containing gaseous compounds (e.g., NO), oxygen-containing mixtures (e.g., $O_2/CO_2$, $O_2/H_2O$, $O_2/H_2O_2/H_2O$), oxy radical generators (e.g., $CH_3OH$, $CH_2O$), hydroxyl radical generators, and the like, or combinations thereof.

In an aspect, the CPO reactant mixture 10 can be characterized by a carbon to oxygen (C/O) molar ratio of less than about 3:1, alternatively less than about 2.6:1, alternatively less than about 2.4:1, alternatively less than about 2.2:1, alternatively less than about 2:1, alternatively less than about 1.9:1, alternatively equal to or greater than about 2:1, alternatively equal to or greater than about 2.2:1, alternatively equal to or greater than about 2.4:1, alternatively equal to or greater than about 2.6:1, alternatively from about 0.5:1 to about 3:1, alternatively from about 0.7:1 to about 2.5:1, alternatively from about 0.9:1 to about 2.2:1, alternatively from about 1:1 to about 2:1, alternatively from about 1.1:1 to about 1.9:1, alternatively from about 2:1 to about 3:1, alternatively from about 2.2:1 to about 3:1, alternatively from about 2.4:1 to about 3:1, or alternatively from about 2.6:1 to about 3:1, wherein the C/O molar ratio refers to the total moles of carbon (C) of hydrocarbons in the reactant mixture divided by the total moles of oxygen ($O_2$) in the reactant mixture.

For example, when the only source of carbon in the CPO reactant mixture 10 is $CH_4$, the $CH_4/O_2$ molar ratio is the same as the C/O molar ratio. As another example, when the CPO reactant mixture 10 contains other carbon sources besides $CH_4$, such as ethane ($C_2H_6$), propane ($C_3H_8$), butanes ($C_4H_{10}$), etc., the C/O molar ratio accounts for the moles of carbon in each compound (e.g., 2 moles of C in 1 mole of $C_2H_6$, 3 moles of C in 1 mole of $C_3H_8$, 4 moles of C in 1 mole of $C_4H_{10}$, etc.). As will be appreciated by one of skill in the art, and with the help of this disclosure, the C/O molar ratio in the CPO reactant mixture 10 can be adjusted along with other reactor process parameters (e.g., temperature, pressure, flow velocity, etc.) to provide for a syngas with a desired composition (e.g., a a syngas with a desired $H_2/CO$ molar ratio). The C/O molar ratio in the CPO reactant mixture can be adjusted to provide for a decreased amount of unconverted hydrocarbons in the syngas. The C/O molar ratio in the CPO reactant mixture 10 can be adjusted based on the CPO effluent temperature in order to decrease (e g, minimize) the unconverted hydrocarbons content of the produced syngas. As will be appreciated by one of skill in the art, and with the help of this disclosure, the C/O molar ratio can be adjusted along with other reactor process parameters (e.g., temperature, pressure, flow velocity, etc.) to provide for a syngas with a desired composition (e.g., a syngas with a desired $H_2/CO$ molar ratio).

The CPO reactant mixture 10 can further comprise steam, and the steam to carbon ratio in the reactant mixture will be discussed in more detail later herein.

The CPO reaction is an exothermic reaction (e.g., heterogeneous catalytic reaction; exothermic heterogeneous catalytic reaction) that is generally conducted in the presence of a CPO catalyst comprising a catalytically active metal, i.e., a metal active for catalyzing the CPO reaction. The catalytically active metal can comprise a noble metal (e.g., Pt, Rh, Ir, Pd, Ru, Ag, and the like, or combinations thereof); a non-noble metal (e.g., Ni, Co, V, Mo, P, Fe, Cu, and the like, or combinations thereof); rare earth elements (e.g., La, Ce, Nd, Eu, and the like, or combinations thereof); oxides thereof; and the like; or combinations thereof. Generally, a noble metal is a metal that resists corrosion and oxidation in a water-containing environment. As will be appreciated by one of skill in the art, and with the help of this disclosure, the components of the CPO catalyst (e.g., metals such as noble metals, non-noble metals, rare earth elements) can be either phase segregated or combined within the same phase.

In an aspect, the CPO catalysts suitable for use in the present disclosure can be supported catalysts and/or unsupported catalysts. In some aspects, the supported catalysts can comprise a support, wherein the support can be catalytically active (e.g., the support can catalyze a CPO reaction). For example, the catalytically active support can comprise a metal gauze or wire mesh (e.g., Pt gauze or wire mesh); a catalytically active metal monolithic catalyst; etc. In other aspects, the supported catalysts can comprise a support, wherein the support can be catalytically inactive (e.g., the support cannot catalyze a CPO reaction), such as $SiO_2$; silicon carbide (SiC); alumina; a catalytically inactive monolithic support; etc. In yet other aspects, the supported catalysts can comprise a catalytically active support and a catalytically inactive support.

In some aspects, a CPO catalyst can be wash coated onto a support, wherein the support can be catalytically active or inactive, and wherein the support can be a monolith, a foam, an irregular catalyst particle, etc.

In some aspects, the CPO catalyst can be a monolith, a foam, a powder, a particle, etc.

Nonlimiting examples of CPO catalyst particle shapes suitable for use in the present disclosure include cylindrical, discoidal, spherical, tabular, ellipsoidal, equant, irregular, cubic, acicular, and the like, or combinations thereof.

In some aspects, the support comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), zirconium oxide ($ZrO_2$), lanthanum (III) oxide ($La_2O_3$), yttrium (III) oxide ($Y_2O_3$), cerium (IV) oxide ($CeO_2$), zeolites, ZSM-5, perovskite oxides, hydrotalcite oxides, and the like, or combinations thereof.

CPO processes, CPO reactors, CPO catalysts, and CPO catalyst bed configurations suitable for use in the present disclosure are described in more detail in U.S. Provisional Patent Application No. 62/522,910 filed Jun. 21, 2017 (International Application No. PCT/IB2018/054475 filed Jun. 18, 2018) and entitled "Improved Reactor Designs for Heterogeneous Catalytic Reactions;" and U.S. Provisional Patent Application No. 62/521,831 filed Jun. 19, 2017 (International Application No. PCT/IB2018/054470 filed Jun. 18, 2018) and entitled "An Improved Process for Syngas Production for Petrochemical Applications;" each of which is incorporated by reference herein in its entirety.

In an aspect, a CPO reactor suitable for use in the present disclosure (e.g., CPO reactor 100) can comprise a tubular reactor, a continuous flow reactor, an isothermal reactor, an adiabatic reactor, a fixed bed reactor, a fluidized bed reactor, a bubbling bed reactor, a circulating bed reactor, an ebullated bed reactor, a rotary kiln reactor, and the like, or combinations thereof.

In an aspect, the CPO reactor 100 comprises a single reaction zone (as opposed to multiple reaction zones). As will be appreciated by one of skill in the art, and with the help of this disclosure, the process for producing methanol as disclosed herein utilizes a single-stage process (which occurs in a single reaction zone) for the production of syngas (as opposed to a multi-stage process for the production of syngas, wherein the multi-stage process occurs in two or more reaction zones). In an aspect, the process for producing methanol as disclosed herein excludes the use of a multi-stage process for the production of syngas. Further, and as will be appreciated by one of skill in the art, and with the help of this disclosure, the syngas 15 recovered from the CPO reactor 100 is not further subjected to additional oxidation or partial oxidation; and the syngas 15 recovered from the CPO reactor 100 is suitable for introduction to the methanol reactor 200 without the need to undergo further oxidation or partial oxidation.

In some aspects, the CPO reactor 100 can be characterized by at least one CPO operational parameter selected from the group consisting of a CPO reactor temperature (e.g., CPO catalyst bed temperature); CPO feed temperature (e.g., CPO reactant mixture temperature); target CPO effluent temperature; a CPO pressure (e.g., CPO reactor pressure); a CPO contact time (e.g., CPO reactor contact time); a C/O molar ratio in the CPO reactant mixture; a steam to carbon (S/C) molar ratio in the CPO reactant mixture, wherein the S/C molar ratio refers to the total moles of water ($H_2O$) in the reactant mixture divided by the total moles of carbon (C) of hydrocarbons in the reactant mixture; and combinations thereof. For purposes of the disclosure herein, the CPO effluent temperature is the temperature of the syngas (e.g., syngas effluent) measured at the point where the syngas exits the CPO reactor (CPO reactor 100), e.g., a temperature of the syngas measured at a CPO reactor outlet, a temperature of the syngas effluent, a temperature of the exit syngas effluent. For purposes of the disclosure herein, the CPO effluent temperature (e.g., target CPO effluent temperature) is considered an operational parameter. As will be appreciated by one of skill in the art, and with the help of this disclosure, the choice of operational parameters for the CPO reactor such as CPO feed temperature; CPO pressure; CPO contact time; C/O molar ratio in the CPO reactant mixture; S/C molar ratio in the CPO reactant mixture; etc. determines the temperature of the CPO reactor effluent (e.g., syngas), as well as the composition of the CPO reactor effluent (e.g., syngas). Further, and as will be appreciated by one of skill in the art, and with the help of this disclosure, monitoring the CPO effluent temperature can provide feedback for changing other operational parameters (e.g., CPO feed temperature; CPO pressure; CPO contact time; C/O molar ratio in the CPO reactant mixture; S/C molar ratio in the CPO reactant mixture; etc.) as necessary for the CPO effluent temperature to match the target CPO effluent temperature. Furthermore, and as will be appreciated by one of skill in the art, and with the help of this disclosure, the target CPO effluent temperature is the desired CPO effluent temperature, and the CPO effluent temperature (e.g., measured CPO effluent temperature, actual CPO effluent temperature) may or may not coincide with the target CPO effluent temperature. In aspects where the CPO effluent temperature is different from the target CPO effluent temperature, one or more CPO operational parameters (e.g., CPO feed temperature; CPO pressure; CPO contact time; C/O molar ratio in the CPO reactant mixture; S/C molar ratio in the CPO reactant mixture; etc.) can be adjusted (e.g., modified) in order for the CPO effluent temperature to match (e.g., be the same with, coincide with) the target CPO effluent temperature. The CPO reactor 100 can be operated under any suitable operational parameters that can provide for a syngas with a desired composition (e.g., a syngas with a desired $H_2/CO$ molar ratio).

The CPO reactor 100 can be characterized by a CPO feed temperature of from about 25° C. to about 600° C., alternatively from about 25° C. to about 500° C., alternatively from about 25° C. to about 400° C., alternatively from about 50° C. to about 400° C., or alternatively from about 100° C. to about 400° C. In aspects where the CPO reactant mixture comprises steam, the CPO feed temperature can be as high as about 600° C., alternatively about 575° C., alternatively about 550° C., or alternatively about 525° C. In aspects where the CPO reactant mixture does not comprise steam, the CPO feed temperature can be as high as about 450° C., alternatively about 425° C., alternatively about 400° C., or alternatively about 375° C.

The CPO reactor 100 can be characterized by a CPO effluent temperature (e.g., target CPO effluent temperature) of equal to or greater than about 300° C., alternatively equal to or greater than about 600° C., alternatively equal to or greater than about 700° C., alternatively equal to or greater than about 750° C., alternatively equal to or greater than about 800° C., alternatively equal to or greater than about 850° C., alternatively from about 300° C. to about 1,600° C., alternatively from about 600° C. to about 1,400° C., alternatively from about 600° C. to about 1,300° C., alternatively from about 700° C. to about 1,200° C., alternatively from about 750° C. to about 1,150° C., alternatively from about 800° C. to about 1,125° C., or alternatively from about 850° C. to about 1,100° C.

In an aspect, the CPO reactor 100 can be characterized by any suitable reactor temperature and/or catalyst bed temperature. For example, the CPO reactor 100 can be characterized by a reactor temperature and/or catalyst bed temperature of equal to or greater than about 300° C., alternatively equal to or greater than about 600° C., alternatively equal to or greater than about 700° C., alternatively equal to or greater than about 750° C., alternatively equal to or greater than about 800° C., alternatively equal to or greater than about 850° C., alternatively from about 300° C. to about 1,600° C., alternatively from about 600° C. to about 1,400° C., alternatively from about 600° C. to about 1,300° C., alternatively from about 700° C. to about 1,200° C., alternatively from about 750° C. to about 1,150° C., alternatively from about 800° C. to about 1,125° C., or alternatively from about 850° C. to about 1,100° C.

The CPO reactor 100 can be operated under any suitable temperature profile that can provide for a syngas with a desired composition (e.g., a syngas with a desired $H_2/CO$ molar ratio). The CPO reactor 100 can be operated under adiabatic conditions, non-adiabatic conditions, isothermal conditions, near-isothermal conditions, etc. For purposes of the disclosure herein, the term "non-adiabatic conditions" refers to process conditions wherein a reactor is subjected to external heat exchange or transfer (e.g., the reactor is heated; or the reactor is cooled), which can be direct heat exchange and/or indirect heat exchange. As will be appreciated by one of skill in the art, and with the help of this disclosure, the terms "direct heat exchange" and "indirect heat exchange" are known to one of skill in the art. By contrast, the term "adiabatic conditions" refers to process conditions wherein a reactor is not subjected to external heat exchange (e.g., the reactor is not heated; or the reactor is not cooled). Generally, external heat exchange implies an external heat exchange system (e.g., a cooling system; a heating system) that requires energy input and/or output. As will be appreciated by one of skill in the art, and with the help of this disclosure, external heat transfer can also result from heat loss from the catalyst bed (or reactor) owing to radiation heat transfer, conduction heat transfer, convection heat transfer, and the like, or combinations thereof. For example, the catalyst bed can participate in heat exchange with the external environment, and/or with reactor zones upstream and/or downstream of the catalyst bed.

For purposes of the disclosure herein, the term "isothermal conditions" refers to process conditions (e.g., CPO operational parameters) that allow for a substantially constant temperature of the reactor and/or catalyst bed (e.g., isothermal temperature) that can be defined as a temperature that varies by less than about +10° C., alternatively less than about +9° C., alternatively less than about +8° C., alternatively less than about +7° C., alternatively less than about +6° C., alternatively less than about +5° C., alternatively less than about +4° C., alternatively less than about +3° C., alternatively less than about +2° C., or alternatively less than about +1° C. across the reactor and/or catalyst bed, respectively.

Further, for purposes of the disclosure herein, the term "isothermal conditions" refers to process conditions (e.g., CPO operational parameters) effective for providing for a syngas with a desired composition (e.g., a desired $H_2/CO$ molar ratio; a desired $CO_2$ content; etc.), wherein the isothermal conditions comprise a temperature variation of less than about +10° C. across the reactor and/or catalyst bed.

The CPO reactor 100 can be operated under any suitable operational parameters that can provide for isothermal conditions.

For purposes of the disclosure herein, the term "near-isothermal conditions" refers to process conditions (e.g., CPO operational parameters) that allow for a fairly constant temperature of the reactor and/or catalyst bed (e.g., near-isothermal temperature), which can be defined as a temperature that varies by less than about +100° C., alternatively less than about +90° C., alternatively less than about +80° C., alternatively less than about +70° C., alternatively less than about +60° C., alternatively less than about +50° C., alternatively less than about +40° C., alternatively less than about +30° C., alternatively less than about +20° C., alternatively less than about +10° C., alternatively less than about +9° C., alternatively less than about +8° C., alternatively less than about +7° C., alternatively less than about +6° C., alternatively less than about +5° C., alternatively less than about +4° C., alternatively less than about +3° C., alternatively less than about +2° C., or alternatively less than about +1° C. across the reactor and/or catalyst bed, respectively. In some aspects, near-isothermal conditions allow for a temperature variation of less than about +50° C., alternatively less than about +25° C., or alternatively less than about +10° C. across the reactor and/or catalyst bed. Further, for purposes of the disclosure herein, the term "near-isothermal conditions" is understood to include "isothermal" conditions.

Furthermore, for purposes of the disclosure herein, the term "near-isothermal conditions" refers to process conditions (e.g., CPO operational parameters) effective for providing for a syngas with a desired composition (e.g., a desired $H_2/CO$ molar ratio; a desired $CO_2$ content; etc.), wherein the near-isothermal conditions comprise a temperature variation of less than about +100° C. across the reactor and/or catalyst bed.

In an aspect, a process as disclosed herein can comprise conducting the CPO reaction under near-isothermal conditions to produce syngas, wherein the near-isothermal conditions comprise a temperature variation of less than about +100° C. across the reactor and/or catalyst bed.

The CPO reactor 100 can be operated under any suitable operational parameters that can provide for near-isothermal conditions.

The CPO reactor 100 can be characterized by a CPO pressure (e.g., reactor pressure measured at the reactor exit or outlet) of equal to or greater than about 1 barg, alternatively equal to or greater than about 10 barg, alternatively equal to or greater than about 20 barg, alternatively equal to or greater than about 25 barg, alternatively equal to or greater than about 30 barg, alternatively equal to or greater than about 35 barg, alternatively equal to or greater than about 40 barg, alternatively equal to or greater than about 50 barg, alternatively less than about 30 barg, alternatively less than about 25 barg, alternatively less than about 20 barg, alternatively less than about 10 barg, from about 1 barg to about 90 barg, alternatively from about 1 barg to about 40 barg, alternatively from about 1 barg to about 30 barg, alternatively from about 1 barg to about 25 barg, alternatively from about 1 barg to about 20 barg, alternatively from about 1 barg to about 10 barg, alternatively from about 20 barg to about 90 barg, alternatively from about 25 barg to about 85 barg, or alternatively from about 30 barg to about 80 barg.

The CPO reactor 100 can be characterized by a CPO contact time of from about 0.001 milliseconds (ms) to about 5 seconds (s), alternatively from about 0.001 ms to about 1 s, alternatively from about 0.001 ms to about 100 ms, alternatively from about 0.001 ms to about 10 ms, alternatively from about 0.001 ms to about 5 ms, or alternatively from about 0.01 ms to about 1.2 ms. Generally, the contact time of a reactor comprising a catalyst refers to the average amount of time that a compound (e.g., a molecule of that compound) spends in contact with the catalyst (e.g., within the catalyst bed), e.g., the average amount of time that it takes for a compound (e.g., a molecule of that compound) to travel through the catalyst bed. For purposes of the disclosure herein the contact time of less than about 5 ms can be referred to as "millisecond regime" (MSR); and a CPO process or CPO reaction as disclosed herein characterized by a contact time of less than about 5 ms can be referred to as "millisecond regime"-CPO (MSR-CPO) process or reaction, respectively.

In some aspects, the CPO reactor 100 can be characterized by a contact time of from about 0.001 ms to about 5 ms, or alternatively from about 0.01 ms to about 1.2 ms.

All of the CPO operational parameters disclosed herein are applicable throughout all of the embodiments disclosed herein, unless otherwise specified. As will be appreciated by one of skill in the art, and with the help of this disclosure, each CPO operational parameter can be adjusted to provide for a desired syngas quality, such as a syngas with a desired composition (e.g., a syngas with a desired $H_2/CO$ molar ratio). For example, the CPO operational parameters can be adjusted to provide for a decreased $CO_2$ content of the syngas. As another example, the CPO operational parameters can be adjusted to provide for an increased $H_2$ content of the syngas. As yet another example, the CPO operational parameters can be adjusted to provide for a decreased unreacted hydrocarbons (e.g., unreacted $CH_4$) content of the syngas.

When excess hydrocarbons (e.g., methane) are present in the CPO reactant mixture 10, a portion of hydrocarbons can undergo a thermal decomposition reaction, for example as represented by equation (2):

$$CH_4 \rightarrow C + 2H_2 \qquad (2)$$

The decomposition reaction of hydrocarbons, such as methane, is facilitated by elevated temperatures, and increases the hydrogen content in the syngas 15. As will be appreciated by one of skill in the art, and with the help of this disclosure, and without wishing to be limited by theory, while the percentage of hydrocarbons in the CPO reactant mixture 10 that undergoes a decomposition reaction (e.g., a decomposition reaction as represented by equation (2)) increases with increasing the C/O molar ratio in the CPO reactant mixture 10, a portion of hydrocarbons can undergo a decomposition reaction to carbon (C) and $H_2$ even at relatively low C/O molar ratios in the CPO reactant mixture 10 (e.g., a C/O molar ratio in the CPO reactant mixture 10 of less than about 2:1). Carbon resulting from hydrocarbon decomposition, for example as represented by equation (2), can be deposited on the CPO catalyst as coke.

In an aspect, the CPO reactant mixture 10 can further comprise a diluent, such as water and/or steam. The CPO reactor 100 can be operated under any suitable operational parameters that can provide for a syngas with a desired composition (e.g., a syngas with a desired $H_2/CO$ molar ratio); for example, the CPO reactor 100 can be operated with introducing water and/or steam to the CPO reactor 100.

Generally, a diluent is inert with respect to the CPO reaction, e.g., the diluent does not participate in the CPO reaction (e.g., a CPO reaction as represented by equation (1)). However, and as will be appreciated by one of skill in the art, and with the help of this disclosure, some diluents (e.g., water, steam, etc.) might undergo chemical reactions other than the CPO reaction within the CPO reactor 100, and can change the composition of the resulting syngas (e.g., syngas 15). As will be appreciated by one of skill in the art, and with the help of this disclosure, water and/or steam can be used to vary the composition of the resulting syngas. Steam can react with methane, for example as represented by equation (3):

$$CH_4 + H_2O \rightleftharpoons CO + 3H_2 \qquad (3)$$

In an aspect, a diluent comprising water and/or steam can increase a hydrogen content of the resulting syngas (e.g., syngas 15). For example, in aspects where the CPO reactant mixture 10 comprises water and/or steam diluent, the resulting syngas (e.g., syngas 15) can be characterized by a hydrogen to carbon monoxide molar ratio that is increased when compared to a hydrogen to carbon monoxide molar ratio of a syngas produced by an otherwise similar process conducted with a reactant mixture comprising hydrocarbons and oxygen without the water and/or steam diluent.

Further, in the presence of water and/or steam in the CPO reactor 100, carbon monoxide can react with the water and/or steam to form carbon dioxide and hydrogen via a water-gas shift (WGS) reaction, for example as represented by equation (4):

$$CO + H_2O \rightleftharpoons CO_2 + H_2 \qquad (4)$$

The WGS reaction can increase the $H_2/CO$ molar ratio of the syngas 15.

When carbon is present in the reactor (e.g., coke; C produced as a result of a decomposition reaction as represented by equation (2)), water and/or steam diluent can react with the carbon and generate additional CO and $H_2$, for example as represented by equation (5):

$$C + H_2O \rightleftharpoons CO + H_2 \qquad (5)$$

Further, since oxygen is present in the CPO reactant mixture 10, the carbon present in the reactor (e.g., coke; C produced as a result of a decomposition reaction as represented by equation (2)) can also react with oxygen, for example as represented by equation (6):

$$C+O_2 \rightarrow CO_2 \qquad (6)$$

As will be appreciated by one of skill in the art, and with the help of this disclosure, although the chemical reactions as represented by equations (5) and (6) can consume a first portion of the carbon produced in the CPO reactor, a second portion of the carbon can be deposited as coke on the CPO catalyst.

Further, $CO_2$ can react with carbon (e.g., coke; C produced as a result of a decomposition reaction as represented by equation (2)), for example as represented by equation (7):

$$C+CO_2 \rightleftharpoons 2\ CO \qquad (7)$$

thereby decreasing the amount of coke deposited on the CPO catalyst. As will be appreciated by one of skill in the art, and with the help of this disclosure, although the reactions as represented by equations (4) and (6) can produce $CO_2$ in the CPO reactor 100, such $CO_2$ may not entirely prevent coke deposition on the CPO catalyst, owing, in part, to $CO_2$ participating in reactions other than the reaction represented by equation (7).

For example, $CO_2$ can react with methane in a dry reforming reaction, for example as represented by equation (8):

$$CH_4+CO_2 \rightleftharpoons 2\ CO+2H_2 \qquad (8)$$

thereby increasing the amount of CO and $H_2$ in the resulting syngas (e.g., syngas 15). Without wishing to be limited by theory, the dry reforming reaction (e.g., as represented by equation (8)) is an endothermic reaction. The dry reforming reaction can remove a portion of the process heat (e.g., heat produced by the exothermic CPO reaction, for example as represented by equation (1)).

In an aspect, the CPO reactor 100 can be operated under near-isothermal conditions, wherein the near-isothermal conditions comprise a temperature variation of less than about +100° C. across the CPO reactor and/or a catalyst bed thereof, wherein the catalyst bed comprises the CPO catalyst, and wherein the single reaction zone comprises the catalyst bed. In an aspect, the CPO reactor 100 can be operated under isothermal conditions, wherein the isothermal conditions comprise a temperature variation of less than about +10° C. across the CPO reactor and/or a catalyst bed thereof, wherein the catalyst bed comprises the CPO catalyst, and wherein the single reaction zone comprises the catalyst bed. In some aspects, the near-isothermal conditions and/or the isothermal conditions can be provided by removal of process heat from the CPO reactor 100. In such aspects, the removal of heat from the CPO reactor 100 can comprise heat removal via an endothermic dry reforming reaction (e.g., as represented by equation (8)) between carbon dioxide and methane.

In an aspect, the CPO reactor 100 can be operated at a steam to carbon (S/C) molar ratio in the CPO reactant mixture of less than about 2.4:1, alternatively less than about 2:1, alternatively less than about 1.5:1, alternatively less than about 1:1, alternatively less than about 0.8:1, alternatively from about 0.01:1 to less than about 2.4:1, alternatively from about 0.05:1 to about 2:1, alternatively from about 0.1:1 to about 1.5:1, alternatively from about 0.15:1 to about 1:1, or alternatively from about 0.2:1 to about 0.8:1, wherein the S/C molar ratio refers to the total moles of water ($H_2O$) in the reactant mixture divided by the total moles of carbon (C) of hydrocarbons in the reactant mixture. As will be appreciated by one of skill in the art, and with the help of this disclosure, the steam that is introduced to the reactor for use as a diluent in a CPO reaction as disclosed herein is present in significantly smaller amounts than the amounts of steam utilized in steam reforming (e.g., SMR) processes, and as such, a process for producing syngas as disclosed herein can yield a syngas with lower amounts of hydrogen when compared to the amounts of hydrogen in a syngas produced by steam reforming.

The S/C molar ratio in the CPO reactant mixture 10 can be adjusted based on the desired CPO effluent temperature (e.g., target CPO effluent temperature) in order to increase (e.g., maximize) the $H_2$ content of the produced syngas. As will be appreciated by one of skill in the art, and with the help of this disclosure, the reaction (3) that consumes steam in the CPO reactor 100 is preferable over the water-gas shift (WGS) reaction (4) in the CPO reactor 100, as reaction (3) allows for increasing the $H_2$ content of the produced syngas, as well as the M ratio of the produced syngas, wherein the M ratio is a molar ratio defined as $(H_2—CO_2)/(CO+CO_2)$.

In an aspect, the amount of methane that reacts according to reaction (3) in the CPO reactor 100 is less than the amount of methane that reacts according to reaction (1) in the CPO reactor 100. In an aspect, less than about 50 mol %, alternatively less than about 40 mol %, alternatively less than about 30 mol %, alternatively less than about 20 mol %, or alternatively less than about 10 mol % of hydrocarbons (e.g., methane) react with steam in the CPO reactor 100.

Without wishing to be limited by theory, the presence of water and/or steam in the CPO reactor 100 changes the flammability of the CPO reactant mixture 10, thereby providing for a wider practical range of C/O molar ratios in the CPO reactant mixture 10. Further, and without wishing to be limited by theory, the presence of water and/or steam in the CPO reactor 100 allows for the use of lower C/O molar ratios in the CPO reactant mixture 10. Furthermore, and without wishing to be limited by theory, the presence of water and/or steam in the CPO reactor 100 allows for operating the CPO reactor 100 at relatively high pressures.

As will be appreciated by one of skill in the art, and with the help of this disclosure, the introduction of water and/or steam in the CPO reactor 100 can lead to increasing the amount of unreacted hydrocarbons in the syngas 15. Further, as will be appreciated by one of skill in the art, and with the help of this disclosure, methanol production processes typically tolerate limited amounts of unreacted hydrocarbons in the syngas.

In some aspects, the syngas 15 can comprise less than about 7.5 mol %, alternatively less than about 5 mol %, or alternatively less than about 2.5 mol % hydrocarbons (e.g., unreacted hydrocarbons, unreacted $CH_4$). In such aspects, the syngas 15 can be produced in a CPO process that employs water and/or steam. In such aspects, the syngas 15 can be used for methanol synthesis.

In an aspect, the syngas 15 can have a $CO_2$ content of less than about 5 mol %, alternatively less than about 4 mol %, alternatively less than about 3 mol %, alternatively less than about 2 mol %, alternatively less than about 1 mol %, alternatively from about 0.1 mol % to about 5 mol %, alternatively from about 0.25 mol % to about 4 mol %, or alternatively from about 0.5 mol % to about 3 mol %. The syngas 15 can be advantageously produced with a $CO_2$ content of less than about 5 mol %, although $CO_2$ (e.g., $CO_2$ stream 13) is being introduced to the CPO reactor 100. A fairly low $CO_2$ content in the syngas 15 can lead to a crude methanol stream 40 having a fairly low water content (e.g., less than about 10 wt. %, alternatively less than about 8 wt. %, alternatively less than about 6 wt. %, alternatively less than about 4 wt. %, alternatively less than about 3 wt. %, alternatively less than about 2 wt. %, or alternatively less than about 1 wt. %, based on the total weight of the crude methanol stream 40). The advantages of a fairly low $CO_2$ content in the syngas 15 and/or a fairly low water content in the crude methanol stream 40 are described in more detail in in the co-pending U.S. Provisional Patent Application Nos. 62/794,783 filed Jan. 21, 2019 and entitled "Methanol Production Process," and 62/787,598 filed Jan. 2, 2019 and entitled "Methanol Production Process;" each of which is incorporated by reference herein in its entirety.

In an aspect, a syngas 15 can be recovered from the CPO reactor 100, wherein the syngas 15 comprises hydrogen, carbon monoxide, water, carbon dioxide, and unreacted hydrocarbons.

In some aspects, the syngas 15 (e.g., subsequent to cooling and water removal from syngas; and/or subsequent to pressure and/or syngas temperature adjustment) can be used in a downstream process (e.g., methanol production) without further processing to enrich the hydrogen content of the syngas 15 (e.g., the syngas 15 is not further processed to enrich the hydrogen content). The syngas 15 as disclosed herein can be characterized by a $H_2/CO$ molar ratio of greater than about 1.7, alternatively greater than about 1.8, alternatively greater than about 1.9, alternatively greater than about 2.0, or alternatively greater than about 2.1. In some aspects, the syngas 15 as disclosed herein can be characterized by a $H_2/CO$ molar ratio of from about 1.7 to about 2.3, alternatively from about 1.8 to about 2.2, or alternatively from about 1.9 to about 2.1.

In an aspect, the syngas 15 can be characterized by an M ratio of from about 1.2 to about 1.8, alternatively from about 1.6 to about 1.78, or alternatively from about 1.7 to about 1.78; wherein the M ratio is a molar ratio defined as $(H_2-CO_2)/(CO+CO_2)$.

In other aspects, the syngas 15 can be further processed prior to using syngas 15 in a downstream process, such as methanol production. The syngas 15 can be processed to enrich its hydrogen content; for example by contacting the syngas 15 with additional (e.g., supplemental) hydrogen (e.g., hydrogen stream 51).

As will be appreciated by one of skill in the art, and with the help of this disclosure, although the syngas 15 can be characterized by a $H_2/CO$ molar ratio of greater than about 1.8, which can be appropriate for methanol synthesis, the syngas 15 can be processed to further increase its hydrogen content. Further, as will be appreciated by one of skill in the art, and with the help of this disclosure, the syngas 15 can be subjected to minimal processing, such as the recovery of unreacted hydrocarbons, diluent, water, etc., without substantially changing the $H_2/CO$ molar ratio of the CPO syngas 15. For example, water can be condensed and separated from the syngas 15, e.g., in a condenser.

In an aspect, a process for producing methanol as disclosed herein can further comprise (i) recovering at least a portion of the unreacted hydrocarbons from the syngas 15 to yield recovered hydrocarbons, and (ii) recycling at least a portion of the recovered hydrocarbons to the CPO reactor 100. As will be appreciated by one of skill in the art, and with the help of this disclosure, although fairly high conversions can be achieved in CPO processes (e.g., conversions of equal to or greater than about 90%), the unconverted hydrocarbons could be recovered and recycled back to the CPO reactor 100.

In aspects where the syngas 15 is characterized by an M ratio of from about 1.8 to about 2.2, the syngas 15 can be further used for methanol production.

In an aspect, a process for producing methanol as disclosed herein can comprise a step of introducing at least a portion of the syngas 15 to the methanol reactor 200 to produce a methanol reactor effluent stream 30; wherein the methanol reactor effluent stream 30 comprises methanol, water, hydrogen, carbon monoxide, carbon dioxide, and hydrocarbons. The methanol reactor 200 can comprise any reactor suitable for a methanol synthesis reaction from CO and $H_2$, such as for example an isothermal reactor, an adiabatic reactor, a trickle bed reactor, a fluidized bed reactor, a slurry reactor, a loop reactor, a cooled multi tubular reactor, and the like, or combinations thereof.

Generally, CO and $H_2$ can be converted into methanol ($CH_3OH$), for example as represented by equation (9):

(9)

$CO_2$ and $H_2$ can also be converted to methanol, for example as represented by equation (10):

(10)

Methanol synthesis from CO, $CO_2$ and $H_2$ is a catalytic process, and is most often conducted in the presence of copper based catalysts. The methanol reactor 200 can comprise a methanol production catalyst, such as any suitable commercial catalyst used for methanol synthesis. Nonlimiting examples of methanol production catalysts suitable for use in the methanol reactor 200 in the current disclosure include Cu, Cu/ZnO, Cu/ThO$_2$, Cu/Zn/Al$_2$O$_3$, Cu/ZnO/Al$_2$O$_3$, Cu/Zr, and the like, or combinations thereof.

In an aspect, a process for producing methanol as disclosed herein can comprise a step of separating at least a portion of the methanol reactor effluent stream 30 into a crude methanol stream 40 and a vapor stream 50; wherein the crude methanol stream 40 comprises methanol and water; wherein the vapor stream 50 comprises hydrogen, carbon monoxide, carbon dioxide, and hydrocarbons. The methanol reactor effluent stream 30 can be separated into the crude methanol stream 40 and the vapor stream 50 in the gas-liquid separator 300, such as a vapor-liquid separator, flash drum, knock-out drum, knock-out pot, compressor suction drum, etc.

In an aspect, the crude methanol stream 40 can comprise water in an amount of less than about 30 wt. %, alternatively less than about 20 wt. %, alternatively less than about 10 wt. %, alternatively less than about 8 wt. %, alternatively less than about 6 wt. %, alternatively less than about 4 wt. %, alternatively less than about 3 wt. %, alternatively less than about 2 wt. %, or alternatively less than about 1 wt. %, based on the total weight of the crude methanol stream 40.

In an aspect, the crude methanol stream 40 can comprise methanol in an amount of equal to or greater than about 70 wt. %, alternatively equal to or greater than about 80 wt. %, alternatively equal to or greater than about 90 wt. %, alternatively equal to or greater than about 92 wt. %, alternatively equal to or greater than about 94 wt. %, alternatively equal to or greater than about 96 wt. %, alternatively equal to or greater than about 97 wt. %, alternatively equal to or greater than about 98 wt. %, or alternatively equal to or greater than about 99 wt. %, based on the total weight of the crude methanol stream 40.

In an aspect, a process for producing methanol as disclosed herein can comprise a step of separating at least a portion of the crude methanol stream 40 in the distillation unit 400 into a methanol stream 45 and a water stream 46, wherein the distillation unit 400 comprises one or more distillation columns. The water stream 46 comprises water and residual methanol. Generally, the one or more distillation columns can separate components of the crude methanol stream 40 based on their boiling points.

In an aspect, the methanol stream 45 can comprise methanol in an amount of equal to or greater than about 95 wt. %, alternatively equal to or greater than about 97.5 wt. %, alternatively equal to or greater than about 99 wt. %, or alternatively equal to or greater than about 99.9 wt. %, based on the total weight of the methanol stream 45.

In an aspect, a process for producing methanol as disclosed herein can comprise a step of separating at least a portion of the vapor stream 50 into a hydrogen stream 51 and a residual gas stream 52, wherein the hydrogen stream 51 comprises at least a portion of the hydrogen of the vapor stream 50, and wherein the residual gas stream 52 comprises carbon monoxide, carbon dioxide, and hydrocarbons. The vapor stream 50 can be separated into the hydrogen stream 51 and the residual gas stream 52 in a hydrogen recovery unit 500, such as a PSA unit, a membrane separation unit, a cryogenic separation unit, and the like, or combinations thereof.

In an aspect, at least a portion 51a of the hydrogen stream 51 can be recycled to the methanol reactor 200, for example via syngas 15.

In an aspect, a process for producing methanol as disclosed herein can comprise a step of separating at least a portion of the residual gas stream 52 in a $CO_2$ separator 600 (e.g., $CO_2$ scrubber) into a $CO_2$ stream 13 and a purge gas stream 60; wherein the $CO_2$ stream 13 comprises at least a portion of the $CO_2$ of the residual gas stream 52; and wherein the purge gas stream 60 comprises carbon monoxide and hydrocarbons.

The $CO_2$ separator 600 can comprise $CO_2$ removal by amine (e.g., monoethanolamine) absorption (e.g., amine scrubbing), pressure swing adsorption (PSA), temperature swing adsorption, gas separation membranes (e.g., porous inorganic membranes, palladium membranes, polymeric membranes, zeolites, etc.), cryogenic separation, and the like, or combinations thereof. In an aspect, the $CO_2$ separator 600 can comprise $CO_2$ removal by amine absorption. As will be appreciated by one of skill in the art, and with the help of this disclosure, a $CO_2$-lean syngas has a higher M ratio than a $CO_2$-rich syngas: the lower the $CO_2$ content of the syngas, the higher the M ratio of the syngas.

In some aspects, at least a portion of the purge gas stream 60 can be purged. In other aspects, at least a portion of the purge gas stream 60 can be used as fuel, for example for pre-heating the CPO reactant mixture 10.

In an aspect, at least a portion of the $CO_2$ stream 13 can be recycled to the CPO reactor 100, for example subsequent to adjusting the temperature and/or pressure of the $CO_2$ stream 13 to desired values. The $CO_2$ introduced to the CPO reactor via the $CO_2$ stream 13 can provide for $CO_2$ that can further reduce or eliminate coke deposits on the CPO catalysts, for example by participating in the reaction represented by equation (7). In an aspect, the amount of carbon deposited on the CPO catalyst can be less than the amount of carbon deposited on a catalyst in an otherwise similar process that does not recycle the $CO_2$ stream to the CPO reactor.

Further, $CO_2$ introduced to the CPO reactor 100 via the $CO_2$ stream 13 can provide for $CO_2$ that can be converted to useful syngas components, such as CO and $H_2$, for example by participating in the dry reforming reaction represented by equation (8).

As will be appreciated by one of skill in the art, and with the help of this disclosure, the reactions represented by equations (7) and (8) reduce the amount of $CO_2$ that will be present in the syngas 15. Further, and as will be appreciated by one of skill in the art, and with the help of this disclosure, and without wishing to be limited by theory, the $H_2$/CO molar ratio of the syngas accounts for the amounts of hydrogen and CO present in the syngas; while the M ratio of the syngas accounts for the carbon dioxide content of the syngas, in addition to the amounts of hydrogen and CO present in the syngas.

In an aspect, a process for producing methanol can comprise the steps of (a) reacting, via a catalytic partial oxidation (CPO) reaction, a CPO reactant mixture 10 in a CPO reactor 100 to produce syngas 15; wherein the CPO reactant mixture 10 comprises hydrocarbons and oxygen; wherein the CPO reactor 100 comprises a CPO catalyst; and wherein the syngas 15 comprises hydrogen ($H_2$), carbon monoxide (CO), carbon dioxide ($CO_2$), water ($H_2O$), and unreacted hydrocarbons; (b) cooling at least a portion of the syngas 15 to yield a cooled syngas and process heat (e.g., which can be recovered and used as thermal energy); (c) removing at least a portion of the water from the cooled syngas to yield a dehydrated syngas, wherein the dehydrated syngas comprises $H_2$, CO, $CO_2$, and unreacted hydrocarbons; (d) introducing at least a portion of the dehydrated syngas to a methanol reactor 200 to produce a methanol reactor effluent stream 30; wherein the methanol reactor effluent stream 30 comprises methanol, water, hydrogen, carbon monoxide, carbon dioxide, and hydrocarbons; (e) separating at least a portion of the methanol reactor effluent stream 30 in a gas-liquid separator 300 into a crude methanol stream 40 and a vapor stream 50, wherein the vapor stream 50 comprises hydrogen, carbon monoxide, carbon dioxide, and hydrocarbons; (f) separating at least a portion of the vapor stream 50 into a hydrogen stream 51 and a residual gas stream 52; wherein the hydrogen stream 51 comprises at least a portion of the hydrogen of the vapor stream 50; and wherein the residual gas stream 52 comprises carbon monoxide, carbon dioxide, and hydrocarbons; (g) separating at least a portion of the residual gas stream 52 in a $CO_2$ separator 600 into a $CO_2$ stream 13 and a purge gas stream 60; wherein the $CO_2$ stream 13 comprises at least a portion of the $CO_2$ of the residual gas stream 52; (h) recycling at least a portion of the $CO_2$ stream 13 to the CPO reactor 100; and (i) recycling at least a portion of the hydrogen stream 51 to the methanol reactor 200. In such aspect, the CPO reactor 100 can be characterized by a near-isothermal temperature.

In an aspect, a process for producing methanol as disclosed herein can advantageously display improvements in one or more process characteristics when compared to an otherwise similar process that does not recycle the $CO_2$ stream to the CPO reactor. The process for producing methanol as disclosed herein can advantageously reduce coke (e.g., carbon) deposits in the CPO reactor, for example coke deposits on the CPO catalyst. A portion of the $CO_2$ stream recycled to the CPO reactor can advantageously react with carbon deposits. As will be appreciated by one of skill in the art, and with the help of this disclosure, a reduced amount of coke deposits on the CPO catalyst can advantageously increase the life-time and productivity of the catalyst.

In an aspect, a portion of the $CO_2$ stream recycled to the CPO reactor can advantageously react with methane via a dry reforming reaction, thereby providing for a near-isothermal operation of the CPO reactor.

As will be appreciated by one of skill in the art, and with the help of this disclosure, since the CPO reaction is exothermic, no additional heat supply in the form of fuel combustion is needed (except for pre-heating reactants in the reaction mixture that is supplied to a syngas generation section), when compared to conventional steam reforming. As such, the process for producing syngas as disclosed herein can advantageously generate less $CO_2$ through fuel burning, when compared to steam reforming.

In an aspect, a process for producing methanol as disclosed herein can advantageously provide for an improved overall carbon utilization (e.g., carbon efficiency), when compared to an otherwise similar process that does not recycle the $CO_2$ stream to the CPO reactor. For purposes of the disclosure herein the carbon efficiency is defined as the ratio of the number of moles of carbon present in the methanol stream (e.g., methanol stream 45) to the number of moles of carbon in the CPO reactant mixture (e.g., CPO reactant mixture 10). Additional advantages of the processes for the production of methanol as disclosed herein can be apparent to one of skill in the art viewing this disclosure.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

ADDITIONAL DISCLOSURE

The following are non-limiting, specific embodiments in accordance with the present disclosure:

A first embodiment, which is a process for producing methanol comprising (a) reacting, via a catalytic partial oxidation (CPO) reaction, a CPO reactant mixture in a CPO reactor to produce syngas; wherein the CPO reactant mixture comprises hydrocarbons, oxygen, and optionally steam; wherein the CPO reactor comprises a single reaction zone, wherein the single reaction zone comprises a CPO catalyst; and wherein the syngas comprises hydrogen ($H_2$), carbon monoxide (CO), carbon dioxide ($CO_2$), water ($H_2O$), and unreacted hydrocarbons, (b) introducing at least a portion of the syngas to a methanol reactor to produce a methanol reactor effluent stream; wherein the methanol reactor effluent stream comprises methanol, water, hydrogen, carbon monoxide, carbon dioxide, and hydrocarbons, (c) separating at least a portion of the methanol reactor effluent stream into a crude methanol stream, a hydrogen stream, a $CO_2$ stream, and a purge gas stream; wherein the crude methanol stream comprises methanol and water; wherein the purge gas stream comprises carbon monoxide and hydrocarbons; and wherein the $CO_2$ stream comprises at least a portion of the $CO_2$ of the methanol reactor effluent stream, and (d) recycling at least a portion of the $CO_2$ stream to the CPO reactor.

A second embodiment, which is the process of the first embodiment, wherein the step (c) further comprises separating at least a portion of the methanol reactor effluent stream in a gas-liquid separator into the crude methanol stream and a vapor stream, wherein the vapor stream comprises hydrogen, carbon monoxide, carbon dioxide, and hydrocarbons.

A third embodiment, which is the process of the second embodiment further comprising separating at least a portion of the vapor stream in a hydrogen recovery unit into the hydrogen stream and a residual gas stream; wherein the hydrogen stream comprises at least a portion of the hydrogen of the vapor stream; and wherein the residual gas stream comprises carbon monoxide, carbon dioxide, and hydrocarbons.

A fourth embodiment, which is the process of the third embodiment further comprising separating at least a portion of the residual gas stream in a $CO_2$ separator into the $CO_2$ stream and the purge gas stream; wherein the $CO_2$ stream comprises at least a portion of the $CO_2$ of the residual gas stream.

A fifth embodiment, which is the process of the fourth embodiment, wherein the $CO_2$ separator comprises $CO_2$ removal by amine absorption, pressure swing adsorption, temperature swing adsorption, gas separation membranes, cryogenic separation, or combinations thereof.

A sixth embodiment, which is the process of any of the first through the fifth embodiments further comprising recycling at least a portion of the hydrogen stream to the methanol reactor.

A seventh embodiment, which is the process of any of the first through the sixth embodiments 6, wherein the hydrocarbons comprise methane, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, or combinations thereof.

An eighth embodiment, which is the process of any of the first through the seventh embodiments, wherein (1) cooling at least a portion of the syngas to yield a cooled syngas; (2) removing at least a portion of the water from the cooled syngas to yield a dehydrated syngas, wherein the dehydrated syngas comprises $H_2$, CO, $CO_2$, and unreacted hydrocarbons; and (3) introducing at least a portion of the dehydrated syngas to the methanol reactor in step (b).

A ninth embodiment, which is the process of any of the first through the eighth embodiments, wherein a portion of the hydrocarbons in the CPO reactant mixture undergo decomposition to carbon and hydrogen.

A tenth embodiment, which is the process of the ninth embodiment, wherein at least a portion of the carbon reacts with carbon dioxide in the CPO reactor to produce carbon monoxide.

An eleventh embodiment, which is the process of any of the ninth and the tenth embodiments, wherein a portion of the carbon is deposited on the CPO catalyst, and wherein the amount of carbon deposited on the CPO catalyst is less than the amount of carbon deposited on a catalyst in an otherwise similar process that does not recycle the $CO_2$ stream to the CPO reactor.

A twelfth embodiment, which is the process of any of the first through the eleventh embodiments, wherein a portion of the hydrocarbons reacts with carbon dioxide in the CPO reactor, via a dry reforming reaction, to produce hydrogen and carbon monoxide.

A thirteenth embodiment, which is the process of any of any of the first through the twelfth embodiments, wherein the CPO reactor is characterized by at least one CPO operational parameter selected from the group consisting of a CPO feed temperature of from about 25° C. to about 600° C.; a CPO effluent temperature of from about 300° C. to about 1,600° C.; a CPO pressure of from about 1 barg to about 90 barg; a CPO contact time of from about 0.001 milliseconds (ms) to about 5 s; a carbon to oxygen (C/O) molar ratio in the CPO reactant mixture of from about 0.5:1 to about 3:1, wherein the C/O molar ratio refers to the total moles of carbon (C) of hydrocarbons in the reactant mixture divided by the total moles of oxygen ($O_2$) in the reactant mixture; a steam to carbon (S/C) molar ratio in the CPO reactant mixture of from about 0.01:1 to less than about 2.4:1, wherein the S/C molar ratio refers to the total moles of water ($H_2O$) in the reactant mixture divided by the total moles of carbon (C) of hydrocarbons in the reactant mixture; and combinations thereof.

A fourteenth embodiment, which is the process of any of the first through the thirteenth embodiments, wherein the CPO reactor is operated under near-isothermal conditions, wherein the near-isothermal conditions comprise a temperature variation of less than about +100° C. across the CPO reactor and/or a catalyst bed thereof, wherein the catalyst bed comprises the CPO catalyst, and wherein the single reaction zone comprises the catalyst bed.

A fifteenth embodiment, which is the process of the fourteenth embodiment, wherein the near-isothermal conditions are provided by removal of process heat from the CPO reactor.

A sixteenth embodiment, which is the process of the fifteenth embodiment, wherein the removal of heat comprises heat removal via an endothermic dry reforming reaction between carbon dioxide and methane.

A seventeenth embodiment, which is a process for producing methanol comprising (a) reacting, via a catalytic partial oxidation (CPO) reaction, a CPO reactant mixture in a CPO reactor to produce syngas; wherein the CPO reactant mixture comprises hydrocarbons and oxygen; wherein the CPO reactor comprises a single reaction zone, wherein the single reaction zone comprises a CPO catalyst; and wherein the syngas comprises hydrogen ($H_2$), carbon monoxide (CO), carbon dioxide ($CO_2$), water ($H_2O$), and unreacted hydrocarbons, (b) cooling at least a portion of the syngas 15 to yield a cooled syngas, (c) removing at least a portion of the water from the cooled syngas to yield a dehydrated syngas, wherein the dehydrated syngas comprises $H_2$, CO, $CO_2$, and unreacted hydrocarbons, (d) introducing at least a portion of the dehydrated syngas to a methanol reactor to produce a methanol reactor effluent stream; wherein the methanol reactor effluent stream comprises methanol, water, hydrogen, carbon monoxide, carbon dioxide, and hydrocarbons, (e) separating at least a portion of the methanol reactor effluent stream in a gas-liquid separator into a crude methanol stream and a vapor stream, wherein the vapor stream comprises hydrogen, carbon monoxide, carbon dioxide, and hydrocarbons, (f) separating at least a portion of the vapor stream into a hydrogen stream and a residual gas stream; wherein the hydrogen stream comprises at least a portion of the hydrogen of the vapor stream; and wherein the residual gas stream comprises carbon monoxide, carbon dioxide, and hydrocarbons, (g) separating at least a portion of the residual gas stream in a $CO_2$ separator into a $CO_2$ stream and a purge gas stream; wherein the $CO_2$ stream comprises at least a portion of the $CO_2$ of the residual gas stream, (h) recycling at least a portion of the $CO_2$ stream to the CPO reactor, and (i) recycling at least a portion of the hydrogen stream to the methanol reactor.

An eighteenth embodiment, which is the process of the seventeen embodiment, wherein at least a portion of the purge gas stream is used as fuel.

A nineteenth embodiment, which is the process of the eighteenth embodiment, wherein at least a portion of the fuel is used for pre-heating at least a portion of the CPO reactant mixture prior to introducing the CPO reactant mixture to the CPO reactor.

A twentieth embodiment, which is the process of any of the seventeenth through the nineteenth embodiments, wherein the CPO reactor is operated under near-isothermal conditions, wherein the near-isothermal conditions comprise a temperature variation of less than about +100° C. across the CPO reactor and/or a catalyst bed thereof, wherein the catalyst bed comprises the CPO catalyst, and wherein the single reaction zone comprises the catalyst bed.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing methanol comprising:
    (a) reacting, via a catalytic partial oxidation (CPO) reaction, a CPO reactant mixture in a CPO reactor to produce syngas; wherein the CPO reactant mixture comprises hydrocarbons, oxygen, and optionally steam; wherein the CPO reactor comprises a single reaction zone, wherein the single reaction zone comprises a CPO catalyst; and wherein the syngas comprises hydrogen ($H_2$), carbon monoxide (CO), carbon dioxide ($CO_2$), water ($H_2$), and unreacted hydrocarbons;
    (b) introducing at least a portion of the syngas to a methanol reactor to produce a methanol reactor effluent stream; wherein the methanol reactor effluent stream comprises methanol, water, hydrogen, carbon monoxide, carbon dioxide, and hydrocarbons;
    (c) separating at least a portion of the methanol reactor effluent stream into a crude methanol stream, a hydrogen stream, a $CO_2$ stream, and a purge gas stream; wherein the crude methanol stream comprises methanol and water; wherein the purge gas stream comprises carbon monoxide and hydrocarbons; and wherein the $CO_2$ stream comprises at least a portion of the $CO_2$ of the methanol reactor effluent stream; and
    (d) recycling at least a portion of the $CO_2$ stream to the CPO reactor.

2. The process of claim 1, wherein the step (c) further comprises separating at least a portion of the methanol reactor effluent stream in a gas-liquid separator into the crude methanol stream and a vapor stream, wherein the vapor stream comprises hydrogen, carbon monoxide, carbon dioxide, and hydrocarbons.

3. The process of claim 2 further comprising the step of separating at least a portion of the vapor stream in a hydrogen recovery unit into the hydrogen stream and a residual gas stream; wherein the hydrogen stream comprises at least a portion of the hydrogen of the vapor stream; and wherein the residual gas stream comprises carbon monoxide, carbon dioxide, and hydrocarbons.

4. The process of claim 3 further comprising the step of separating at least a portion of the residual gas stream in a $CO_2$ separator into the $CO_2$ stream and the purge gas stream; wherein the $CO_2$ stream comprises at least a portion of the C0 of the residual gas stream.

5. The process of claim 4, wherein the $CO_2$ separator comprises $CO_2$ removal by amine absorption, pressure swing adsorption, temperature swing adsorption, gas separation membranes, cryogenic separation, or combinations thereof.

6. The process of claim 1 further comprising the step of recycling at least a portion of the hydrogen stream to the methanol reactor.

7. The process of claim 1, wherein the hydrocarbons comprise methane, natural gas, natural gas liquids, associated gas, well head gas, enriched gas, paraffins, shale gas, shale liquids, fluid catalytic cracking (FCC) off gas, refinery process gases, stack gases, fuel gas from fuel gas header, or combinations thereof.

8. The process of claim 1, wherein (1) cooling at least a portion of the syngas to yield a cooled syngas; (2) removing at least a portion of the water from the cooled syngas to yield a dehydrated syngas, wherein the dehydrated syngas comprises $H_2$, CO, $CO_2$, and unreacted hydrocarbons; and (3) introducing at least a portion of the dehydrated syngas to the methanol reactor in step (b).

9. The process of claim 1, wherein a portion of the hydrocarbons in the CPO reactant mixture undergo decomposition to carbon and hydrogen.

10. The process of claim 9, wherein at least a portion of the carbon reacts with carbon dioxide in the CPO reactor to produce carbon monoxide.

11. The process of claim 9, wherein a portion of the carbon is deposited on the CPO catalyst, and wherein the amount of carbon deposited on the CPO catalyst is less than the amount of carbon deposited on a catalyst in an otherwise similar process that does not recycle the $CO_2$ stream to the CPO reactor.

12. The process of claim 1, wherein a portion of the hydrocarbons reacts with carbon dioxide in the CPO reactor, via a dry reforming reaction, to produce hydrogen and carbon monoxide.

13. The process of claim 1, wherein the CPO reactor further includes at least one CPO operational parameter selected from the group consisting of a CPO feed temperature of from about 25° C. to about 600° C.; a CPO effluent temperature of from about 300° C. to about 1,600° C.; a CPO pressure of from about 1 barg to about 90 barg; a CPO contact time of from about 0.001 milliseconds (ms) to about 5 s; a carbon to oxygen (C/O) molar ratio in the CPO reactant mixture of from about 0.5:1 to about 3:1, wherein the C/O molar ratio refers to the total moles of carbon (C) of hydrocarbons in the reactant mixture divided by the total moles of oxygen (0) in the reactant mixture; a steam to carbon (S/C) molar ratio in the CPO reactant mixture of from about 0.01:1 to less than about 2.4:1, wherein the S/C molar ratio refers to the total moles of water ($H_2O$) in the reactant mixture divided by the total moles of carbon (C) of hydrocarbons in the reactant mixture; and combinations thereof.

14. The process of claim 1, wherein the CPO reactor is operated under near-isothermal conditions, wherein the near-isothermal conditions comprise a temperature variation of less than about +100° C. across the CPO reactor and/or a catalyst bed thereof, wherein the catalyst bed comprises the CPO catalyst, and wherein the single reaction zone comprises the catalyst bed.

15. The process of claim 14, wherein the near-isothermal conditions are provided by removal of process heat from the CPO reactor.

16. The process of claim 15, wherein the removal of heat comprises heat removal via an endothermic dry reforming reaction between carbon dioxide and methane.

17. A process for producing methanol comprising:
(a) reacting, via a catalytic partial oxidation (CPO) reaction, a CPO reactant mixture in a CPO reactor to produce syngas; wherein the CPO reactant mixture comprises hydrocarbons and oxygen; wherein the CPO reactor comprises a single reaction zone, wherein the single reaction zone comprises a CPO catalyst; and wherein the syngas comprises hydrogen ($H_2$), carbon monoxide (CO), carbon dioxide ($CO_2$), water ($H_2O$), and unreacted hydrocarbons;
(b) cooling at least a portion of the syngas to yield a cooled syngas;
(c) removing at least a portion of the water from the cooled syngas to yield a dehydrated syngas, wherein the dehydrated syngas comprises $H_2$, CO, $CO_2$, and unreacted hydrocarbons;
(d) introducing at least a portion of the dehydrated syngas to a methanol reactor to produce a methanol reactor effluent stream; wherein the methanol reactor effluent stream comprises methanol, water, hydrogen, carbon monoxide, carbon dioxide, and hydrocarbons;
(e) separating at least a portion of the methanol reactor effluent stream in a gas-liquid separator into a crude methanol stream and a vapor stream, wherein the vapor stream comprises hydrogen, carbon monoxide, carbon dioxide, and hydrocarbons;
(f) separating at least a portion of the vapor stream into a hydrogen stream and a residual gas stream; wherein the hydrogen stream comprises at least a portion of the hydrogen of the vapor stream; and wherein the residual gas stream comprises carbon monoxide, carbon dioxide, and hydrocarbons;
(g) separating at least a portion of the residual gas stream in a $CO_2$ separator into a $CO_2$ stream and a purge gas stream; wherein the $CO_2$ stream comprises at least a portion of the $CO_2$ of the residual gas stream;
(h) recycling at least a portion of the $CO_2$ stream to the CPO reactor; and
(i) recycling at least a portion of the hydrogen stream to the methanol reactor.

18. The process of claim 17, wherein at least a portion of the purge gas stream is used as fuel.

19. The process of claim 18, wherein at least a portion of the fuel is used for pre-heating at least a portion of the CPO reactant mixture prior to introducing the CPO reactant mixture to the CPO reactor.

20. The process of claim 17, wherein the CPO reactor is operated under near-isothermal conditions, wherein the near-isothermal conditions comprise a temperature variation of less than about +100° C. across the CPO reactor and/or a catalyst bed thereof, wherein the catalyst bed comprises the CPO catalyst, and wherein the single reaction zone comprises the catalyst bed.

\* \* \* \* \*